US00PP19331P2

(12) United States Plant Patent
van Opstal

(10) Patent No.: US PP19,331 P2
(45) Date of Patent: Oct. 14, 2008

(54) ***PIERIS* PLANT NAMED 'RALTO'**

(50) Latin Name: *Pieris japonica*
Varietal Denomination: Ralto

(76) Inventor: Ronnie Adrianus Antonius van Opstal, St. Willebrordusstraat 3, 4882 NM Zundert (NL)

( * ) Notice: Subject to any disclaimer, the term of this patent is extended or adjusted under 35 U.S.C. 154(b) by 0 days.

(21) Appl. No.: 11/974,216

(22) Filed: Oct. 11, 2007

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV–ROM search for PBR 20050570 search for cultivar Ralto p. 1.*

* cited by examiner

*Primary Examiner*—Annette H Para
(74) *Attorney, Agent, or Firm*—C. A. Whealy

(57) ABSTRACT

A new and distinct cultivar of *Pieris* plant named 'Ralto', characterized by its upright and outwardly spreading plant habit; green and yellow variegated leaves; large inflorescences with numerous red purple-colored flowers; and good garden performance.

2 Drawing Sheets

Botanical designation: *Pieris japonica.*
Cultivar denomination: 'Ralto'.

BACKGROUND OF THE INVENTION

The present Invention relates to a new and distinct cultivar of *Pieris,* botanically known as *Pieris japonica,* and herinafter referred to by the name 'Ralto'.

The new *Pieris* is a naturally-occurring branch mutation of the *Pieris japonica* cultivar Valley Valentine, not patented. The new *Pieris* was discovered and selected by the Inventor from within a population of plants of the cultivar Valley Valentine in a controlled environment in Zundert, The Netherlands in January, 2001.

Asexual reproduction of the new *Pieris* by cuttings taken in a controlled environment in Zundert, The Netherlands since January, 2001 has shown that the unique features of this new *Pieris* are stable and reproduced true to type in successive generations.

SUMMARY OF THE INVENTION

The new *Pieris* has not been observed under all possible environmental conditions. The phenotype may vary somewhat with variations in environment such as temperature and/or light intensity without, however, any variance in genotype. The following traits have been repeatedly observed and are determined to be the unique characteristics of 'Ralto'. These characteristics in combination distinguish 'Ralto' as a new and distinct cultivar of *Pieris:*

1. Upright and outwardly spreading plant habit.
2. Green and yellow variegated leaves.
3. Large inflorescences with numerous red purple-colored flowers.
4. Good garden performance.

Plants of the new *Pieris* differ from plants of the parent, the cultivar Valley Valentine, primarily in leaf color as plants of the cultivar Valley Valentine have solid green-colored leaves.

Plants of the new *Pieris* can be compared to the plants of the *Pieris* cultivar Flaming Silver, not patented. In side-by-side comparisons conducted in Zundert, The Netherlands, plants of the new *Pieris* differed from plants of the cultivar Flaming Silver in the following characteristics:

1. Developing leaves of plants of the new *Pieris* were light green with light orange-colored apices whereas developing leaves of plants of the cultivar Flaming Silver were red in color.
2. Flowers of plants of the new *Pieris* were red purple in color whereas flowers of plants of the cultivar Flaming Silver were creamy white in color.

BRIEF DESCRIPTION OF THE PHOTOGRAPHS

The accompanying colored photographs illustrate the overall appearance of the new *Pieris.* These photographs show the colors as true as it is reasonably possible to obtain in colored reproductions of this type. Colors in the photographs may differ slightly from the color values cited in the detailed botanical description, which accurately describe the colors of the new *Pieris.*

The photograph on the first sheet comprises a side perspective view of a typical flowering plant of 'Ralto' grown in a container.

The photograph on the second sheet is a close-up view of a typical leaves and flowers of 'Ralto'.

DETAILED BOTANICAL DESCRIPTION

The aforementioned photographs and following observations and measurements describe plants grown in Zundert, The Netherlands in 23-cm containers, in a glass-covered greenhouse during the winter and under commercial production conditions. During the production of the plants, day temperatures ranged from 10° C. to 22° C. and night temperatures ranged from 7° C. to 13° C. Plants used for the photographs and description were about five years old. In the following description, color references are made to The Royal Horticultural Society Colour Chart, 2001 Edition, except where general terms of ordinary dictionary significance are used.

Botanical classification: *Pieris japonica* 'Ralto'.

Parentage: Naturally-occurring branch mutation of the *Pieris japonica* cultivar Valley Valentine, not patented.

Propagation:

*Type.*—By cuttings.

*Time to initiate roots, winter.*—About ten weeks at temperatures of 18° C.

*Root description.*—Fine, fibrous; light brown in color.

*Rooting habit.*—Moderate branching; moderately dense.

Plant description:

*Plant form and growth habit.*—Perennial, evergreen; upright and outwardly spreading plant habit; broad inverted triangle. Moderately vigorous growth habit.

*Branching habit.*—Freely branching habit; about six lateral branches develop per plant.

*Plant height, soil level to top of flowers.*—About 40.5 cm.

*Plant diameter, area of spread.*—About 39 cm.

*Lateral branch description.*—Length: About 13.3 cm. Diameter: About 4 mm. Internode length: About 3 mm. Strength: Strong. Texture: Smooth, glabrous. Color: 144A; becoming closer to 199A to 199B with development.

*Foliage description.*—Arrangement: Alternate or whorled at terminals; simple. Length: About 4.6 cm. Width: About 1.6 cm. Shape: Oblanceolate. Apex: Apiculate. Base: Attenuate. Margin: Crenate. Venation pattern: Pinnate. Texture, upper and lower surfaces: Smooth, glabrous. Color: Developing foliage, upper surface: 144A; towards the apex, between 29D and 159A. Developing foliage, lower surface: 144A; towards the apex, 159A. Fully expanded foliage, upper surface: Between 139A and 147A; random blotches, 194A to 194B; margins (about 2 mm in width), between 10B and 10D; venation, 144A. Fully expanded foliage, lower surface: Between 137C and 147B; random blotches, 148D; margins (about 2 mm in width), 8B; venation, 144A. Petiole: Length: About 8 mm. Diameter: About 1 mm. Texture, upper and lower surfaces: Smooth, glabrous. Color, upper and lower surfaces: 146A to 146B.

Flower description:

*Flower arrangement and appearance.*—Single urceolate flowers arranged on terminal paniculate racemes. Inflorescences bending with the weight of developing flowers. Freely flowering habit; about 200 flowers develop per inflorescence during the flowering period.

*Natural flowering season.*—Plants of the new *Pieris* typically flower in March in The Netherlands. Flowers not persistent.

*Flower longevity.*—Individual flowers last about two weeks on the plant.

*Fragrance.*—Sweet, pleasant.

*Inflorescence length.*—About 9.8 cm.

*Inflorescence diameter.*—About 10.6 cm.

*Flower diameter.*—About 6 mm.

*Flower depth.*—About 7 cm.

*Flower bud.*—Length: About 4 mm. Diameter: About 3 mm. Shape: Ovoid. Color: N185C to N185D; towards the apex, 187A to 187B.

*Petals.*—Arrangement: Single urceolate flower form; single whorl of five petals fused at the base. Length: About 6.5 mm. Width: About 3 mm. Shape: Roughly ovate with obtuse apex. Margin: Entire. Texture, upper and lower surfaces: Smooth, glabrous. Color: When opening, upper and lower surfaces: Between 59B to 60B; towards the base, between N155C and 186D. Fully opened, upper and lower surfaces: 60A to 60B; towards the base, between N155C and 186D.

*Sepals.*—Arrangement: Five fused in a single whorl. Length: About 3.5 mm. Width: About 1.2 mm. Shape: Ovate. Apex: Acute. Base: Broadly cuneate. Texture, upper and lower surfaces: Smooth, glabrous. Color: Immature, upper and lower surfaces: N185C to N185D. Mature, upper and lower surfaces: Between N185D and 186D.

*Peduncles.*—Length: About 7.3 cm. Diameter: About 1.4 mm. Angle: Initially upright to about 80° from vertical. Strength: Moderately strong. Texture: Smooth, glabrous. Color, upper surface: 183C to 183D. Color, lower surface: 144B.

*Pedicels.*—Length: About 4 mm. Diameter: Less than 1 mm. Angle: About 10° to 50° from vertical. Strength: Moderately strong. Texture: Smooth, glabrous. Color, upper surface: 144B. Color, lower surface: 183C to 183D.

*Reproductive organs.*—Androecium: Quantity per flower: About ten. Anther shape: Roughly oval. Anther length: About 1 mm. Anther color: 200C to 200D. Pollen amount: Scarce. Pollen color: Close to N167C. Gynoecium: Quantity of pistils per flower: Typically one. Pistil length: About 6 mm. Style length: About 5 mm. Style color: 145B. Stigma shape: Narrowly club-shaped. Stigma diameter: Less than 1 mm. Stigma color: Close to 144B. Ovary color: 144A.

*Seed/fruit.*—Seed and fruit development have not been observed.

Garden performance: Plants of the new *Pieris* have been observed to have good garden performance and to be tolerant to rain and wind and temperatures from about −15° C. to about 33° C.

Disease/pest resistance: Plants have not been observed to be resistant to pathogens and pests common to *Pieris*.

It is claimed:

1. A new and distinct cultivar of *Pieris* plant named 'Ralto' as illustrated and described.

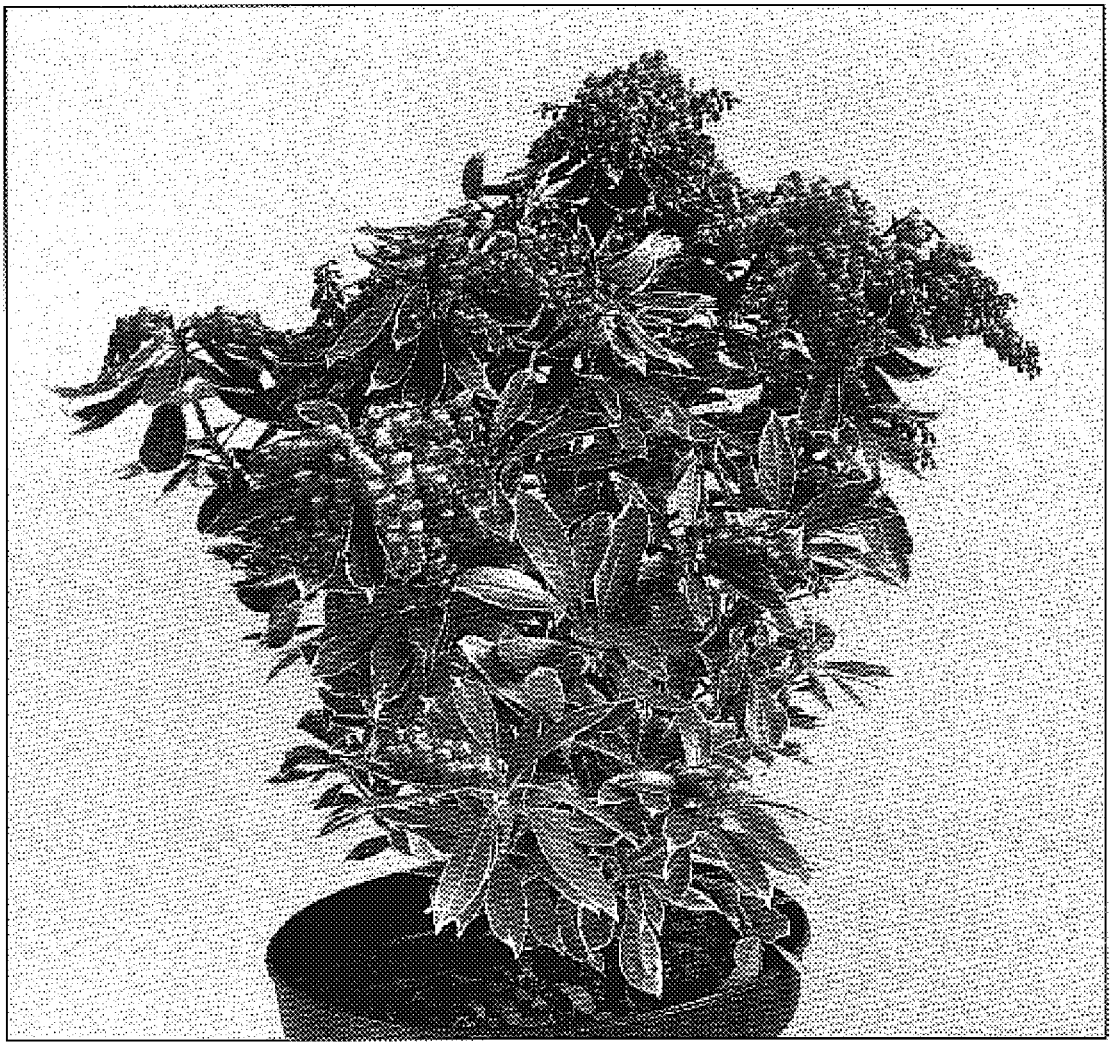

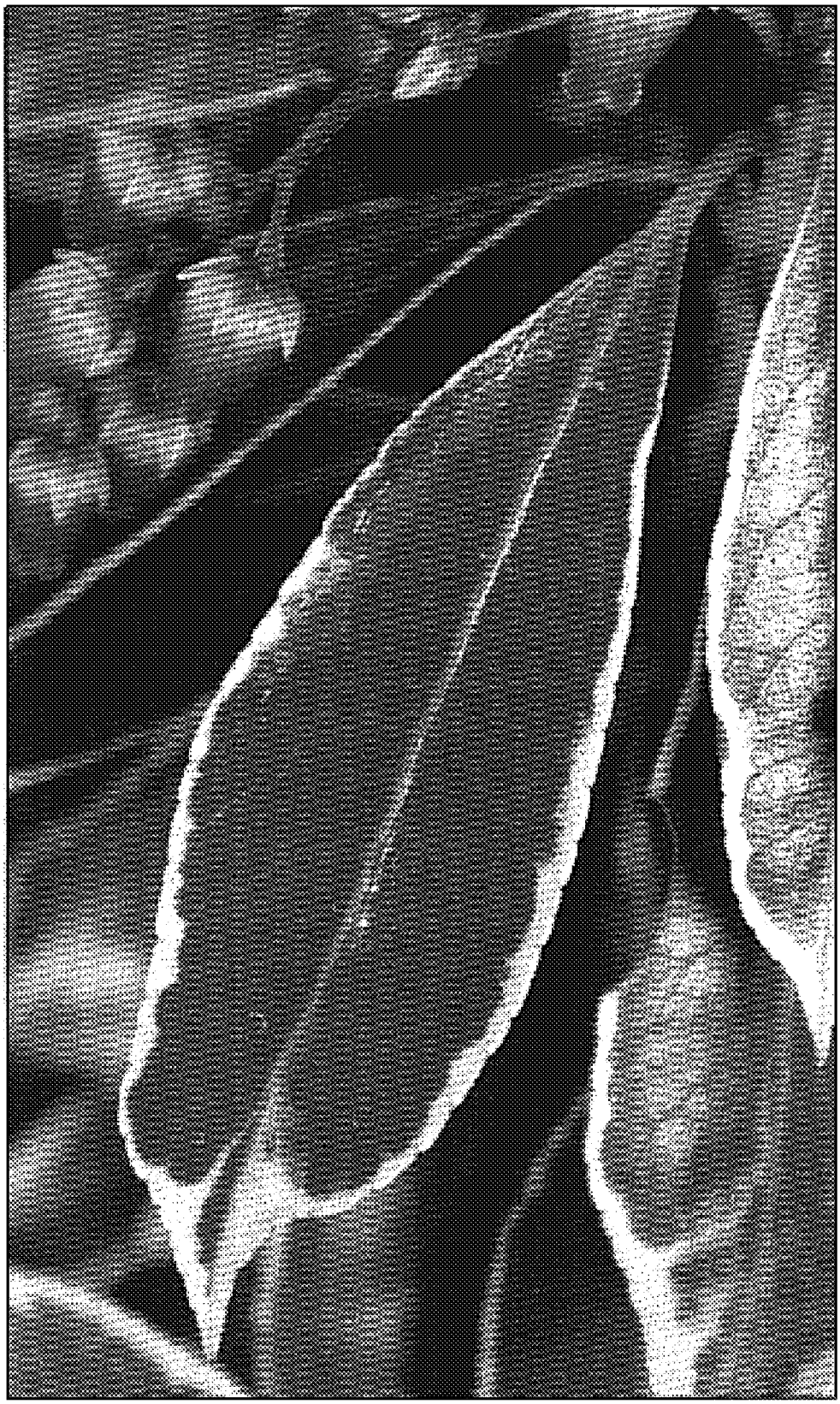

* * * * *